United States Patent [19]

Buzza

[11] 4,297,903
[45] Nov. 3, 1981

[54] LIQUID TRANSFER VALVE

[75] Inventor: Edmund E. Buzza, Fullerton, Calif.

[73] Assignee: Beckman Instruments, Inc., Fullerton, Calif.

[21] Appl. No.: 143,238

[22] Filed: Apr. 24, 1980

[51] Int. Cl.³ .......................................... G01N 35/08
[52] U.S. Cl. ................................. 73/864.22; 137/551; 141/346
[58] Field of Search ............. 73/423 A, 423 R, 422 R, 73/422 GC

[56] References Cited

U.S. PATENT DOCUMENTS

| | | | |
|---|---|---|---|
| 3,266,322 | 8/1966 | Negersmith et al. | 73/423 A |
| 3,552,212 | 1/1971 | Öhlin | 73/423 A |
| 3,747,412 | 7/1973 | Jones | 73/423 A |
| 3,754,443 | 8/1973 | Harris, Sr. et al. | 73/422 GC |
| 3,858,450 | 1/1975 | Jones | 73/423 A |
| 3,911,749 | 10/1975 | Hendry | 73/423 A |
| 3,985,166 | 10/1976 | Klee | 73/422 GC X |
| 3,991,055 | 11/1976 | Godin et al. | 73/422 R X |
| 4,022,065 | 5/1977 | Ramin et al. | 73/422 GC |
| 4,068,528 | 1/1978 | Gudelfinger | 73/422 GC |

Primary Examiner—Daniel M. Yasich
Attorney, Agent, or Firm—R. J. Steinmeyer; J. E. Vanderburgh; Timothy R. Schulte

[57] ABSTRACT

A liquid transfer valve including movable valve portions. A second valve portion is movable with respect to a first valve portion to allow a probe to extend therethrough to pick up a sample liquid. Upon probe retraction, the second valve portion is movable to a position which allows the sample liquid to be injected into the valve where it is diluted and carried to a remote detector or delivery point.

9 Claims, 4 Drawing Figures

LIQUID TRANSFER VALVE

BACKGROUND OF THE INVENTION

1. Field of the Invention

The invention relates to the field of measuring and testing instruments. More particularly, the invention relates to the field of liquid sample handling in measuring and testing instruments. In still greater particularity, the invention is a liquid transfer valve which is utilized with a movable probe. By way of further characterization but not by way of limitation thereto, the invention is a valve having a movable portion and a stationary portion which, in one position, allows the movable probe to access a sample substance and, in a second position, allows the sample substance to be ejected from the probe, combined with a diluent in a fixed ratio, and delivered to a remote location.

2. Description of the Related Art

Measuring and testing instruments utilizing automated sample handling devices may be complex to build and operate when a number of liquids are to be moved to various locations. These instruments normally require that a sample fluid be diluted with a second fluid or reactant before being subjected to testing. This dilution must be accomplished quickly in order to allow a large number of samples to be tested. It may also be desirable to introduce calibration standards into the system at various time intervals. In addition, while washing of the probe is necessary to prevent contamination of subsequent sample liquids, this washing should be accomplished quickly and easily. To minimize the time required to complete these functions it is desirable to minimize the amount of system movement required.

Prior devices such as that shown in U.S. Pat. No. 3,747,412 issued to A. R. Jones on July 24, 1973 employ valves which include sections movable with respect to one another. The apparatus described in the above referenced U.S. Patent is a trapped volume device in which the probe is connected to a movable valve portion. A sample liquid is drawn through the probe and into the valve where a predetermined volume of the sample liquid is trapped. The sample liquid is combined with a fixed volume of another liquid after movement of the valve portions which align conduits connected to sources of these other liquids. While suited for its intended purpose, this device does not allow probe movement with respect to the valves and washing of the probe must be accomplished in a separate step. In addition, the device is complicated and requires much supporting hardware.

SUMMARY OF THE INVENTION

The invention is a liquid transfer valve which is employed with a movable probe. The valve includes a first stationary valve portion and a second movable valve portion. Movement of the valve portions with respect to one another into a first configuration, hereinafter designated as pickup position, allows the probe to move through these valve portions to pick up a sample liquid. After retraction of the probe through the movable valve portions, movement of the movable valve portion into a second position, hereinafter referred to as delivery position, allows the sample liquid to be injected into a passageway where it is mixed with another liquid.

In the pickup position a first access port in the first valve portion and a clearance hole in the second valve portion are aligned, allowing passage of the probe therethrough. Upon retraction of the probe, the second valve portion moves with respect to the first valve portion such that a passageway in the second valve portion is aligned with the first access port in the first valve portion. A conduit in the first valve portion communicates with the first access port and this conduit is connected to a source of diluent or reactant. In the delivery position the sample liquid is delivered from the probe into the first access port at the same time a diluent is delivered through the conduit at a predetermined ratio. These liquids are comingled and the mixture is transported to a detector or remote location through the passageway in the second valve portion. A seal in the first access port contacts the probe to seal and cleanse the outside of the probe upon its retraction from the pickup position. Suitable valving external to the liquid transfer valve allows liquids to be dispensed through the conduit and through the probe to dilute samples, add and dilute calibration standards, and wash both the probe and the valve portions. The dispensed solution is then conducted through the passageway in the second valve portion and delivered to detectors or other remote locations. Sample pickup, delivery, dilution, calibration, and washing of the probe and valve is thereby accomplished with minimum probe and valve movement thereby simplifying these operations.

DESCRIPTION OF THE PREFERRED EMBODIMENT

Figure 1:
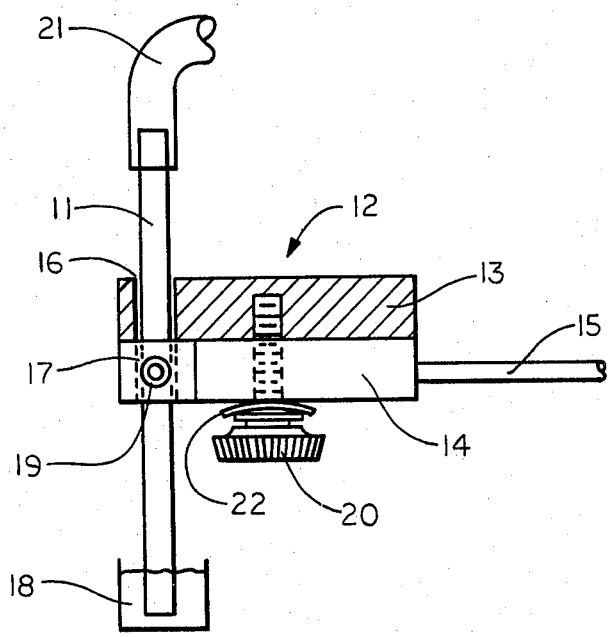
FIG. 1 is a side partially sectioned view of the probe and liquid transfer valve in accordance with the present invention.

Referring to FIG. 1, a probe 11 extends through a liquid transfer valve 12. Valve 12 includes a first valve portion 13 and a second valve portion 14. A driving rod 15 is connected to second portion 14. Driving rod 15 is also connected to a conventional driving source such as a stepper motor (not shown). Probe 11 passes through an access port 16 in first valve portion 13 and a clearance hole 17 (illustrated by the dotted lines in second valve portion 14). Probe 11 is insertable into a sample liquid 18. A passageway 19 extends through second valve portion 14 as will later be described. Probe 11 is connectable to a suitable pumping and valving system by flexible tube 21. First valve portion 13 and second valve portion 14 are biased together by a spring 22 employed with a connector 20. Connector 20 allows rotational movement of second portion 14 with respect to first portion 13.

Figure 2:
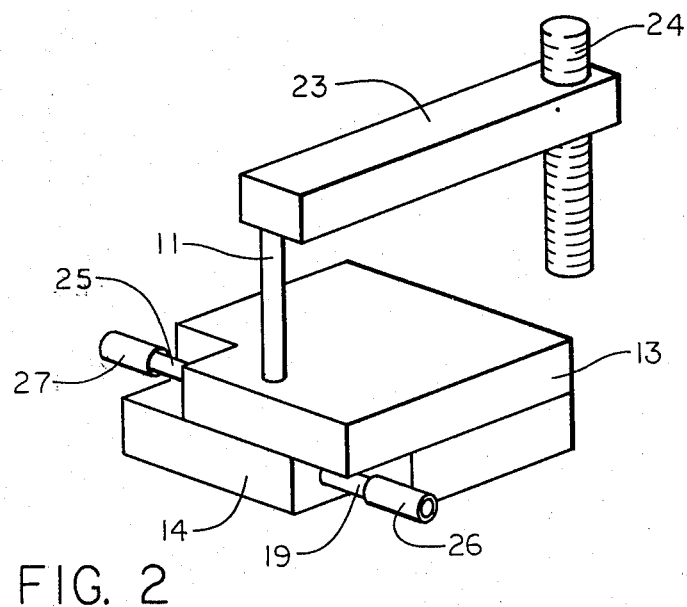
FIG. 2 is a perspective view of the probe and liquid transfer vessel.

Referring to FIG. 2, probe 11 is shown connected to an elevator mechanism which includes a supporting portion 23 and a threaded rod 24. Threaded rod 24 is journaled in a conventional driving mechanism (not shown) to allow probe 11 to be raised and lowered. Passageway 19 extends into second valve portion 14. A conduit 25 extends through first valve portion 13 as will later be described. Passageway 19 is connected to a suitable detector, remote station, or waste container by flexible tube 26. Conduit 25 is connected to a suitable valving and pumping system by flexible tube 27.

Figure 3:
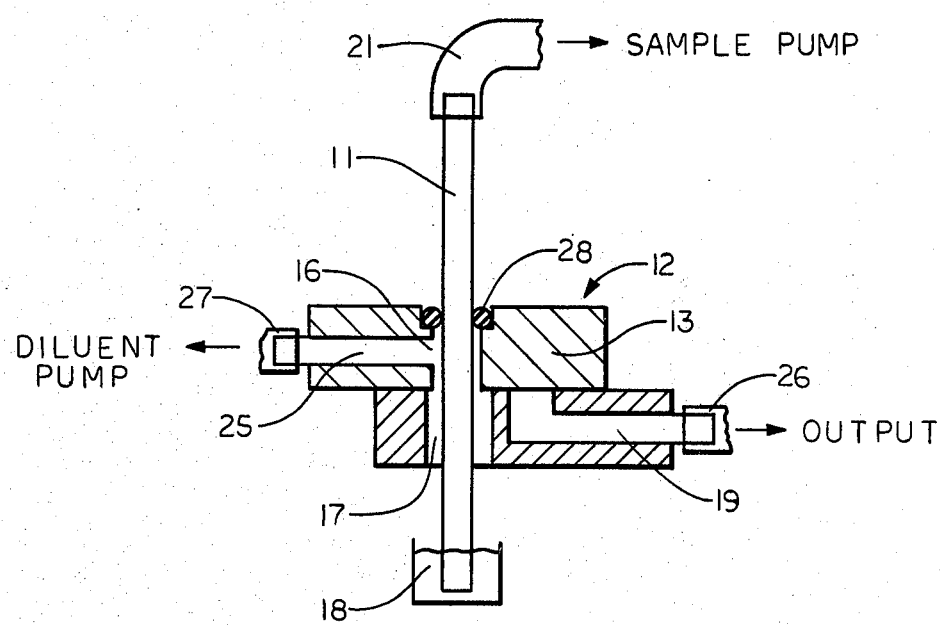
FIG. 3 is a sectioned view of the liquid transfer valve in the pickup position.

Referring to FIG. 3, probe 11 and liquid transfer valve 12 are shown in the pickup position. That is, probe 11 extends through a seal 28, access port 16, and second access port 17 and into sample liquid 18. Conduit 25 communicates with access port 16. Passageway 19 is effectively sealed from communication with access port 16. Probe 11 is connected to a sample pump (not shown) by flexible tube 21.

Figure 4:
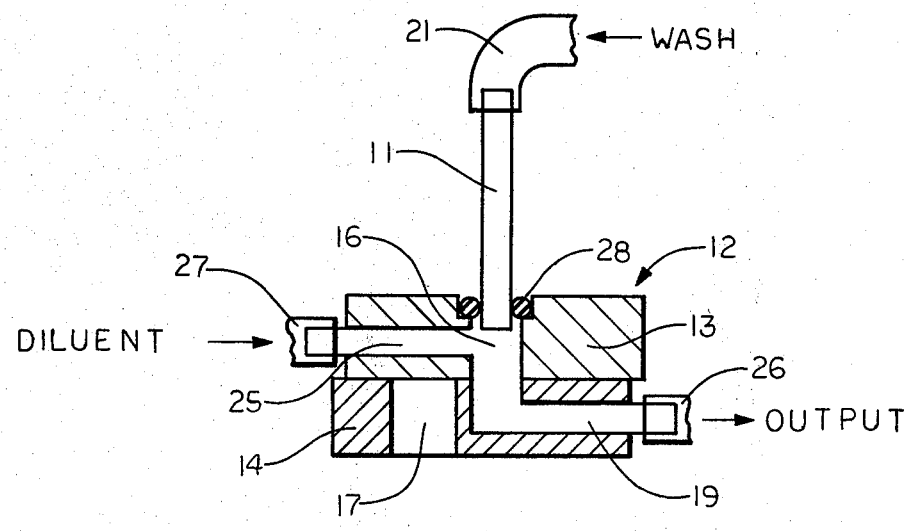
FIG. 4 is a sectioned view of the liquid transfer valve in the delivery position.

Referring to FIG. 4, probe 11 and liquid transfer valve 12 are shown in the delivery position. That is, probe 11 has been retracted such that its tip is positioned in access port 16 and second valve portion 14 has been rotated such that passageway 19 communicates with access port 16. Clearance hole 17 is effectively sealed from access port 16. Conduit 25 communicates with access port 16. Seal 28 contacts probe 11 and first valve portion 13. Probe 11 is connected to a pump system through suitable valving by flexible tube 21.

MODE OF OPERATION

Referring to FIGS. 1 and 3, second valve portion 14 is in the pickup position such that access port 16 and clearance hole 17 are aligned in a plane parallel to the direction of travel of probe 11 thus allowing probe 11 to access sample liquid 18. This position for probe 11 is referred to as the pickup position. In this position, probe 11 picks up sample liquid 18 which is aspirated therein by a sample pump connected to flexible tube 21. Second valve portion 14 is rotatable on connector 20 which is spring loaded to bias second valve portion 14 against first valve portion 13. Driving rod 15 is used to rotate second valve portion 14 into the desired positions.

Referring to FIG. 2, after the sample liquid has been picked up probe 11 is raised by the elevator mechanism. Second valve portion 14 is then rotated by driving rod 15 to the position shown in FIG. 4. The position of probe 11 and second valve portion 14 shown in FIG. 4 is referred to as the delivery position. That is, sample liquid 18 taken into probe 11 is delivered into access port 16 while, at the same time, a diluent liquid is delivered to access port 16 through conduit 25. The sample liquid and diluent liquid pass downward into passageway 19 where they mix and are carried through flexible tube 26 to a desired location. The raising of probe 11 into the delivery position serves to cleanse the outside of probe 11 as it passes seal 28. That is, contact of probe 11 with seal 28 removes any sample liquid remaining on the outside of probe 11. In the delivery position sample liquids, calibration standards, or wash liquid may be dispensed into probe 11 through flexible tube 21 while, at the same time, a diluent or wash liquid is dispensed through flexible tube 27 into conduit 25. Thus, probe 11, conduit 25, and access port 16 may be washed and the wash solution is conducted through passageway 19 and flexible tube 26 thereby also washing them. The diluent and wash solutions may contain reactants, calibration standards, or substances compatible to the desired analysis or sample handling. The valve logic may also deliver only undiluted sample, wash solution, or diluent in the delivery position.

Because a minimal amount of movement is required to pick up, dilute, and deliver a sample liquid or standard, a significant saving in time and accessory apparatus is achieved. In addition, the probe and valve may be washed while in the delivery position. Thus, rotation of second valve portion 14 into the pickup position shown in FIG. 3 and lowering of probe 11 is all that is required to begin another sample dilution. Unnecessary motion is thus eliminated. Probe 11 is only required to move vertically to pick up sample liquids 18 from movable containers. Also, in the pickup position probe 11 may aspirate slugs of air before and/or after the sample to separate it from other liquid that may be in probe 11 or flexible tubing 21. Also, while in the pickup position, a reversible diluent pump connected to flexible tube 27 may aspirate air slugs if so desired. While in the delivery position, these air slugs may be delivered along with the liquids if such is desired.

Advantages of the liquid transfer valve include the elimination of leaky or worn septums. There is no dripping of sample liquid from outside of the probe as it passes through a septum. Also, the device enables air slugs to be drawn into the probe and/or the diluent line and dead valve space is minimized resulting in a low hold-up volume. Also, no stirring is required for mixing of the sample liquid and the diluent liquid because the liquid flow through passageway 19 is sufficient to mix the liquids. The device also allows calibration standards to be easily introduced into the system.

While particular forms of the invention have been disclosed with respect to a preferred embodiment thereof, it is not to be so limited as changes and modifications may be made without departing from the scope of the invention. For example, more than one conduit could be employed in first valve portion 13 if more than one liquid is desired to be combined with the sample liquid. In addition, more than one passageway in second valve portion 14 could be provided such that delivery of diluted sample liquid could be accomplished to multiple locations. Any number of conduits and passageways could be employed without departing from the inventive concept. Additionally, while second valve portion 14 was rotatably mounted to first valve portion 13, it would be possible to mount second valve portion 14 such that it would slide into the pickup and delivery positions. Another possibility would be to have lower portion 14 hinged such that it could drop away from first portion 13 to allow probe access through portion 13. Upon probe retraction, second portion 14 would be again positioned adjacent first portion 13 in the delivery position. Thus only passageway 19 would be required in second valve portion 14 eliminating the need for second access port 17.

The foregoing description, taken together with the appended claims, constitutes a disclosure which enables one skilled in the art and having the benefit of the teachings contained therein to make and use the invention. Further, the structure herein described constitutes a meritorious advance in the art which is unobvious to such skilled workers not having the benefit of these teachings.

What is claimed is:

1. A liquid transfer valve for use with a probe, said probe being movable relative to said valve in a plane of travel toward and away from said valve, said valve comprising:
   a first valve portion including an access port extending through said first valve portion approximately parallel to said plane of travel to allow probe movement therethrough, said first valve portion also including at least one conduit communicating with said access port; and at least one movable valve portion mounted on said first valve portion for relative movement to a pickup position and a delivery position;

said movable second valve portion including a clearance hole extending through said movable valve portion approximately parallel to said plane of travel, said clearance hole aligned with said access port in said pickup position to allow probe movement therethrough; and said movable valve portion further including at least one passageway communicating with said access port in said delivery position.

2. Apparatus according to claim 1 wherein said movable valve portion is rotatably mounted on said first valve portion.

3. Apparatus according to claim 1 wherein said movable valve portion is movably mounted on said first valve portion such that a liquid tight seal is effected.

4. Apparatus according to claim 1 wherein said conduit is connectible to a source of diluent.

5. Apparatus according to claim 1 further including a seal mounted within said access port for contact with said probe.

6. A liquid transfer valve for use in conjunction with a sample probe, said probe being movable with respect to said valve in a plane of travel toward and away from said valve, said valve comprising:

a first valve portion including an access port extending through said first valve portion approximately parallel to said plane of travel to allow probe movement therethrough, said first valve portion also including at least one conduit communicating with said access port; and a second valve portion movably mounted adjacent said first valve portion for movement to a pickup position and a delivery position;

said second valve portion including a clearance hole extending through said second valve portion approximately parallel to said plane of travel to allow probe movement therethrough, said clearance hole alignable with said access port in said pickup position; and said second valve portion further including at least one passageway communicating with said access port in said delivery position.

7. Apparatus according to claim 6 wherein said first valve portion includes a seal mounted within said access port for contact with said probe.

8. Apparatus according to claim 6 wherein said second valve portion is rotatably mounted on said first valve portion.

9. Apparatus according to claim 6 wherein said second valve portion is slidably mounted relative to said first valve portion.

* * * * *